United States Patent [19]

Sorrentino et al.

[11] Patent Number: 4,927,634
[45] Date of Patent: May 22, 1990

[54] PHARMACEUTICAL COMPOSITIONS CONTAINING DYCLONINE HCl AND PHENOL

[75] Inventors: James V. Sorrentino, Wilton; William J. Kelleher, Storrs; Jeanne O. Moye, Fairfield, all of Conn.

[73] Assignee: Richardson-Vicks Inc., Wilton, Conn.

[21] Appl. No.: 297,450

[22] Filed: Jan. 13, 1989

Related U.S. Application Data

[63] Continuation of Ser. No. 133,834, Dec. 16, 1987, Pat. No. 4,808,410.

[51] Int. Cl.$^5$ ............................................. A61N 25/00
[52] U.S. Cl. ..................................... 424/405; 424/464; 424/465; 424/440; 514/317
[58] Field of Search ............... 514/317, 817, 818, 816; 424/464, 465, 405, 440

[56] References Cited

U.S. PATENT DOCUMENTS

| | | | |
|---|---|---|---|
| 2,771,391 | 11/1956 | Bockstahler | 514/817 |
| 2,868,689 | 1/1959 | Florestano et al. | 424/464 |
| 4,139,627 | 2/1979 | Lane et al. | 424/464 |
| 4,508,724 | 4/1985 | Taylor, Jr. et al. | 514/317 |

OTHER PUBLICATIONS

Federal Register, vol. 47, No. 101, Proposed Rules, pp. 22796–22830.
Physicians' Desk Reference for Non-Prescription Drugs, 8th ed., 1987, pp. 518–519.
Chemical Abstr., 88:83979r, 1978, pp. 74–75.

Primary Examiner—Thurman K. Page
Attorney, Agent, or Firm—David K. Dabbiere; Douglas C. Mohl; Jack D. Schaeffer

[57] ABSTRACT

Novel pharmaceutical compositions of matter are disclosed for use in eliciting a topical anesthetic and antimicrobial response, preferably for oral health care purposes, said compositions comprising dyclonine hydrochloride and phenol. When used in combination, dyclonine hydrochloride and phenol provide an improved antimicrobial response.

1 Claim, No Drawings

PHARMACEUTICAL COMPOSITIONS CONTAINING DYCLONINE HCl AND PHENOL

This is a continuation of application Ser. No. 133,834, filed on Dec. 16, 1987 now U.S. Pat. No. 4,808,410.

BACKGROUND OF THE INVENTION

This invention is directed to pharmaceutical compositions containing dyclonine hydrochloride (HCl) and phenol.

Dyclonine HCl, chemically denoted as 3-piperidino-4'-butoxypropiophenone hydrochloride, is a well known anesthetic/analgesic agent for topical use on the mucous membranes of the mouth and throat (see Federal Register, Vol. 47, No. 101, Proposed Rules, pages 22810-13, 1982). Oral pharmaceutical compositions of dyclonine HCl commercially available in the United States include an aqueous liquid spray containing 0.1% dyclonine HCl and solid lozenges containing 1.2 mg dyclonine HCl per lozenge for children and 3.0 mg per lozenge for adults (see Physicians' Desk Reference for Nonprescription Drugs, 8th Ed., 1987, pages 518-9). The benefit of dyclonine HCl is that it provides long acting topical anesthetic relief. The use of certain acids, particularly citric acid, to stabilize dyclonine HCl in anesthetic lozenges is reported in U.S. Pat. No. 4,139,627.

In addition to its anesthetic/analgesic properties, dyclonine HCl is known to possess antimicrobial activity. In this regard, U.S. Pat. No. 2,868,689 discloses stabilized aqueous preparations of dyclonine HCl (0.1–5%) having topical anesthetic and antimicrobial action, the stabilization aspect being provided by the addition of chlorobutanol (0.1–0.5%).

It is noted, for purposes of the subject invention, that phenol was specifically identified in said U.S. Pat. No. 2,868,689 as being an unsatisfactory stabilizer (column 1, lines 60–61).

Phenol is a known topical anesthetic, which has been used to treat minor sore mouth and sore throat pain. The mode of action, fast acting but not long lasting, is that it desensitizes sensory nerve receptors present in the mucous membranes of the throat and oral cavity to exert its local anesthetic effort. Previous dosage forms of administration have included lozenges containing 32.5 mg phenol per lozenge and aqueous solutions of 1.4% phenol for use as a mouthwash, rinse or gargle, which is expelled from the oral cavity after use, and as a throat spray (see Physicians' Desk Reference for Nonprescription Drugs, 8th Ed., 1987, pages 654-5). In addition to its anesthetic activity, phenol is known to possess antimicrobial activity.

It has now been found that the combined action of dyclonine HCl and phenol in pharmaceutical compositions containing an effective topical anesthetic and antimicrobial amount of each active results in producing an enhanced antimicrobial effect beyond that which might be expected from the mere additive effect of the two actives. Without being bound to such explanation, it would seem, in view of the antimicrobial activity of each active, that said antimicrobial enhancement results from co-potentiation between the two, that is, by each active potentiating the antimicrobial activity of the other.

DESCRIPTION OF THE INVENTION

More specifically, the subject invention provides a pharmaceutical composition of matter for topical anesthetic and improved antimicrobial activities. Said composition, although primarily directed to oral health care types of formulations and uses therefor, may also be applicable to other pharmaceutical embodiments for topical usage wherein the enhanced antimicrobial co-action of the two actives would be beneficial, for example in pharmaceutical compositions concerned with skin or hair case usages such as lotions, creams, ointments, gels, shampoos, soaps and the like, wherein antimicrobial activity is desired. In general, the subject composition contains from about 0.02 to about 3.0 weight/weight (w/w) percent of dyclonine HCl and from about 0.3 to about 5.0 w/w percent of phenol in admixture with a pharmaceutically acceptable carrier.

In its primary application, the subject invention provides a pharmaceutical composition of matter for oral health care use which not only provides relief of pain in irritated mucous membranes of the mouth and throat, but also provides enhanced antimicrobial activity. As used herein, the term "oral" includes the throat and oral cavity with contiguous mucosal tissues. Accordingly, the composition of this invention has beneficial application in treating, for example, sore or bacteria infected throat, cough-irritated sore throat, and other oral ailments wherein the source of irritation is partly or wholly derived from microbial infection. Said composition comprises an orally acceptable pharmaceutical carrier having incorporated therein an orally effective topical anesthetic and antimicrobial amount each of dyclonine hydrochloride and of phenol.

It has been found that the composition of this invention possesses antimicrobial action that is greater than the sum of that possessed by dyclonine HCl or phenol when used alone. The enhanced antimicrobial action between dyclonine HCl and phenol is demonstrated in the following type experiment using *Staphylococcus aureus*, a gram-positive bacterium.

METHODOLOGY

A five milliliter (ml) aliquot of the test formulation is dispensed into a clean 18 mm borosilicate glass test tube for the undiluted sample. Dilutions of the test formulation are prepared using sterile deionized water.

The inoculum suspension is prepared from an overnight growth of the challenge organism on appropriate media. In the case of *S. aureus*, Soybean Casein Digest Agar (SCDA) in used. SCDA contains 15 grams/liter (g/L) Soybean Casein Digest Broth and 15 g/L agar. One liter of the medium is autoclaved at 15 psi and 121° C. for 30–40 minutes and approximately 25 ml per plate are poured into sterile disposable 100×15 mm polystyrene Petri dishes. Surface growth from the overnight culture is transferred from the plate using a sterile wire loop to 6 ml of 0.85% sterile saline in a test tube. The suspension is adjusted to an optical density at 540 nanometers ($OD_{540}$) of 0.5 as read in a Spectronic 20 spectrophotometer. This $OD_{540}$ is equivalent to approximately $5 \times 10^8$ colony forming units (cfu)/ml for *S. aureus*. The inoculum size is confirmed by serial dilution of the inoculum into Letheen broth and by plating dilutions onto SCDA using a spread plate technique.

At time zero 0.05 ml of a suspension of the challenge organism is inoculated into each tube and the contents mixed to yield a level of about $5 \times 10^6$ cfu/ml.

At given time intervals 0.1 ml aliquots are removed from each test sample and plated onto SCDA.

All plates are incubated at 30° C. in a convection incubator for 48 hours at which time colonies are counted and cfu/ml are calculated and recorded.

The enhanced antimicrobial effect of phenol and dyclonine HCl in aqueous pharmaceutical preparations is illustrated in Table I by the indicated test results obtained in accordance with the Methodology. The "Base Vehicle" and other test products are described hereinafter in Example 1. The Staphylococcus organism used is *S. aureus* ATCC 6538 (ATCC=American Tissue Culture Collection). In this particular experiment, the actual $OD_{540}$ reading was 0.43 and the actual inoculum size was $5.7 \times 10^6$ cfu/ml. The symbol "P" represents phenol, and the symbol "D" represents dyclonine hydrochloride. The numerical symbols indicate the recorded cfu/ml at the indicated time interval as follows:

TABLE I

| Test Formulation | Dilution | Time (min.) 0.5 | 1 | 3 | 5 |
|---|---|---|---|---|---|
| Base Vehicle | 1x | 4 | 2 | 1 | 0 |
|  | ½x | 4 | 4 | 4 | 4 |
| Base Vehicle with 1.0% w/v P | 1x | 0 | 0 | 0 | 0 |
|  | ½x | 1 | 0 | 0 | 0 |
|  | ¼x | 4 | 4 | 4 | 3 |
| Base Vehicle with 1.4% w/v P | 1x | 0 | 0 | 0 | 0 |
|  | ½x | 0 | 0 | 0 | 0 |
|  | ¼x | 4 | 3 | 2 | 1 |
| Base Vehicle with 0.1% w/v D | 1x | 3 | 1 | 0 | 0 |
|  | ½x | 4 | 4 | 4 | 4 |
|  | ¼x | 4 | 4 | 4 | 4 |
| Base Vehicle with 1.0% w/v P and 0.1% w/v D | 1x | 0 | 0 | 0 | 0 |
|  | ½x | 0 | 0 | 0 | 0 |
|  | ¼x | 4 | 4 | 3 | 0 |
| Base Vehicle with 1.4% w/v P and 0.1% w/v D | 1x | 0 | 0 | 0 | 0 |
|  | ½x | 0 | 0 | 0 | 0 |
|  | ¼x | 0 | 0 | 0 | 0 |

0 = <10 cfu/ml
1 = 10–100 cfu/ml
2 = 101–1000 cfu/ml
3 = 1001–10000 cfu/ml
4 = >$10^4$ cfu/ml Test results show that the Base Vehicle itself has very little antimicrobial effectiveness. Complete kill (0=<10 cfu/ml) is only seen after 5 minutes at full strength (1x) concentration.

Test product containing 1.4% phenol shows complete kill by 30 seconds at full strength concentration and a two-fold dilution (½x). However, a four-fold dilution (¼x) shows less antimicrobial effectiveness with a count of 10–100 cfu/ml being recorded even after 5 minutes.

Test product containing 0.1% dyclonine HCl shows some activity at full strength with complete kill by 3 minutes. However, no activity is recorded at either two-fold or four fold dilutions.

Test product with both 1.4% phenol and 0.1% dyclonine HCl shows complete kill by 30 seconds at full strength, two-fold dilution and four-fold dilution. At the four-fold dilution, the combination product has a faster onset of action than either of the single entity products. The test results demonstrate that the two actives together have more than an additive effect on the antimicrobial activity of the formulations.

Test product containing both 1.0% phenol and 0.1% dyclonine HCl shows a similar effect. With 1.0% phenol alone, diluted four-fold, a 1001–10,000 cfu/ml count is observed after 5 minutes; and the four-fold dilution of dyclonine HCl alone shows no effect. In contrast, the four-fold dilution of the combination of the two actives shows complete kill by 5 minutes.

It is thus shown that marked enhancement exists since the two actives when acting in combination, each in a certain concentration for a certain time and under certain conditions on a fixed number of microorganisms, decrease the number to a lower level than did either of the actives acting alone at the concentration in which it was present in the combination and under the same conditions.

In addition to the aforementioned *S. aureus*, similar evidence of enhancement between the two actives may be observed against other bacterial organisms such as, for example, *Pseudomonas aeruginosa, Hemophilus influenza* and *Neisseria meningitidis*; and yeast, *Candida albicans*.

The present invention thus provides a novel pharmaceutical composition of matter, primarily for oral health care use, wherein it is sought to elicit an antimicrobial response. In addition, the combination of the two actives provides the benefit of both faster acting topical anesthetic activity attributable to the phenol and longer acting topical anesthetic activity attributable to the dyclonine HCl, particularly for the relief of sore throat or mouth conditions requiring anti-microbial treatment. Said composition comprises the two essential active ingredients, dyclonine hydrochloride and phenol in admixture with a pharmaceutically acceptable carrier. In another aspect, the present invention provides a method of enhancing or hastening the onset of antimicrobial activity in a mammal requiring same, preferably for oral health care purposes, said method comprising administering to said mammal an effective anesthetic and antimicrobial amount of dyclonine hydrochloride and phenol sufficient to enhance or hasten the onset of the antimicrobial response.

In preparing the pharmaceutical compositions of the present invention, the dyclonine HCl and phenol are incorporated into a liquid or solid pharmaceutically acceptable carrier according to conventional pharmaceutical practices. The most preferred carrier is an aqueous-based pharmaceutically acceptable carrier, that is, one wherein the entire or predominant solvent content is water. As noted in U.S. Pat. No. 2,868,689, however, dyclonine HCl demonstrates instability in such water-containing preparations and, accordingly, the use of a stabilizer for dyclonine HCl, such as the chlorobutanol referred to therein, or an acid, will serve to prolong and enhance shelf life. Preferably, the pH of the subject compositions utilizing an aqueous-based orally acceptable pharmaceutical carrier will be from about 3 to about 4 and, most preferably, from about 3.2 to about 3.6. To provide and maintain the subject compositions at such pH levels, acid buffers consistent with conventional pharmaceutical practices are generally utilized such as, for example, citrate buffers, phosphate buffers, and the like.

As noted previously, stabilized aqueous pharmaceutical compositions containing dyclonine HCl are heretofore known as, for example, in U.S. Pat. No. 2,868,689, incorporated herein by reference. Accordingly, in a stable liquid pharmaceutical composition for oral health care use comprising an aqueous-based orally acceptable pharmaceutical carrier having incorporated therein an effective topical anesthetic and antimicrobial amount of dyclonine HCl, the present invention provides the improvement comprising the incorporation therein of the herein mentioned amounts of phenol.

In liquid preparations for oral health care purposes, it is common practice to include such product enhancing optional additives as colorants, flavorants, co-solvents and the like, which additives may affect the total solubility of the two actives in the final product. Accordingly, such a liquid composition of the invention having an aqueous-based orally acceptable pharmaceutical carrier preferably has from about 0.05 to about 2.0 weight-/volume (w/v) percent of dyclonine HCl and from about 0.5 to about 3.0 and more preferably from about 1.0 to about 1.4 w/v percent of phenol incorporated into said carrier.

In solid form for oral health care purposes, the present invention may be typically embodied as a lozenge, troche, drop or other similar form which requires the user's saliva action for dissolution of the particular form and to provide topical application of the two essential actives directly to the mouth and throat areas. The preparation of such solid pharmaceutical unit dosage forms are within the routine skill of those in the pharmaceutical art. For example, a conventional candy base suitable for lozenges is heated to the melting point, and the two essential actives, dyclonine hydrochloride and phenol, together with optional ingredients, are intimately mixed therein. In lozenge form, from about 1 to about 3 milligrams of dyclonine hydrochloride and from about 10 to about 50 milligrams, and more preferably from about 20 to about 35 milligrams, of phenol is preferred for each lozenge.

As noted previously, certain acid-stabilized lozenges containing dyclonine HCl are shown and claimed in U.S. Pat. No. 4,139,627, incorporated herein by reference. Accordingly, in a lozenge comprising an anesthetically effective amount of dyclonine HCl and an amount of a pharmaceutically acceptable acid sufficient to stabilize said dyclonine HCl intimately mixed in a hard candy base, the present invention provides the improvement comprising the intimate admixture therein of the herein mentioned amounts of of phenol.

The compositions of this invention may optionally contain one or more other known therapeutic agents, particularly those commonly utilized in oral health care preparations, such as, for example, other agents having local anesthetic or antimicrobial activity. Other optional ingredients which are non-therapeutic and well known to the pharmacist's art may also be included in amounts generally known for such ingredients, for example, natural or artificial sweeteners, flavoring agents, colorants and the like to provide a palatable and pleasant looking final product; ethyl alcohol, propylene glycol, glycerin an the like as co-solvents; and other typical pharmaceutically acceptable ingredients commonly employed in compositions of this type.

The following examples illustrate the Base Vehicle and test products utilized in the experiments herein reported and also illustrate embodiments of the present invention. Example 1

| Ingredients | Base Vehicle (% w/v) |
| --- | --- |
| Citric acid, anhydrous | 0.175 |
| Sodium citrate, dihydrate | 0.038 |
| Ethyl alcohol, 95%* | 10.000 |
| Propylene glycol* | 20.000 |
| Glycerin | 10.000 |
| Sorbitol solution, 70% | 8.600 |
| Sodium saccharin | 0.030 |

-continued

| Ingredients | Base Vehicle (% w/v) |
| --- | --- |
| Flavorant | 0.400 |
| Colorants | 0.010 |
| Phenol | — |
| Dyclonine HCl | — |
| Water, purified . . . q.s. to . . . | 100.000 |
| pH | 3.4 |

*The indicated amount is v/v.

The foregoing formulation represents the herein mentioned Base Vehicle, which is an aqueous-based orally acceptable pharmaceutical carrier without either the dyclonine HCl or the phenol. To this Base Vehicle, 1.0% and 1.4% w/v of phenol (P) are added to provide the herein mentioned two respective test products with phenol as the sole active; and 0.1% w/v of dyclonine HCl (D) is added to provide the herein mentioned test product with dyclonine HCl as the sole active. In addition, both phenol and dyclonine HCl are added to the Base Vehicle in the indicated percentages to provide the herein mentioned two respective test products with both P and D as combined actives, i.e., two respective embodiments of the compositions of this invention.

EXAMPLE 2

The antimicrobial effectiveness of combined phenol and dyclonine HCl on the yeast microorganism, *Candida albicans,* is demonstrated in Table II, the indicated test results being obtained in accordance with the previously described Methodology with the following modifications. The $OD_{540}$ of 0.5 is approximately equivalent to $5 \times 10^7$ cfu/ml for *C. albicans*. In this particular experiment, the actual $OD_{540}$ was 0.63 and the actual inoculum size was $1.8 \times 10^5$. The particular microorganism is *C. albicans* ATCC 10231. Other indicated symbols are as previously denoted.

TABLE II

| Test Formulation | Dilution | Time (min.) | | | |
| --- | --- | --- | --- | --- | --- |
| | | 0.5 | 1 | 3 | 5 |
| Base Vehicle | 1x | 4 | 4 | 4 | 4 |
| | ½x | 4 | 4 | 4 | 4 |
| Base Vehicle with 1.0% w/v P | 1x | 1 | 0 | 0 | 0 |
| | ½x | 4 | 4 | 4 | 4 |
| Base Vehicle with 1.4% w/v P | 1x | 0 | 0 | 0 | 0 |
| | ½x | 4 | 4 | 3 | 2 |
| Base Vehicle with 0.1% w/v D | 1x | 4 | 4 | 4 | 4 |
| | ½x | 4 | 4 | 4 | 4 |
| Base Vehicle with 1.0% w/v P with 0.1% w/v D | ½x | 4 | 3 | 1 | 0 |
| Base Vehicle with 1.4% w/v P and 0.1% w/v D | ½x | 3 | 1 | 0 | 0 |

As shown in the tabulated data, neither 0.1% dyclonine HCl alone nor 1.0% phenol alone show activity at two-fold dilution; and 1.4% phenol alone at this dilution shows slight activity at 3 to 5 minutes. In contrast, the combination of the two actives with 1.0% phenol at the same dilution shows a marked increase in organism kill at 3 minutes and complete kill at 5 minutes; and the combination with 1.4% phenol at the same dilution shows a marked increase in organism kill at 1 minute and complete kill at 3 minutes.

EXAMPLE 3

This example illustrates the composition of this invention in lozenge form.

| Ingredient | Amount/Lozenge | | |
|---|---|---|---|
| | A | B | C |
| Dyclonine HCl | 3.00 | 1.20 | 2.40 mg |
| Phenol | 20.00 | 32.50 | 35.00 mg |
| Citric Acid, anhydrous | 20.40 | 20.40 | 20.40 mg |
| Flavorant | 12.42 | 12.42 | 12.42 mg |
| Colorant | 0.22 | 0.22 | 0.22 mg |
| Anhydrous Candy Base, q.s. to | 2.40 | 2.40 | 2.40 gm |

The candy base is melted in a vacuum cooker and the coloring agent is added. The citric acid is next added and mixed well. The remaining ingredients are then added and the mixture poured on a kneading table, kneaded approximately seven minutes and lozenges then formed.

We claim:

1. A pharmaceutical composition of matter having enhanced antimicrobial action comprising from about 0.02 to about 3.0 w/w percent of dyclonine HCl and from about 0.3 to about 5.0 w/w percent of phenol in admixture with a pharmaceutically acceptable aqueous carrier.

* * * * *